United States Patent [19]

Al-Hakim et al.

[11] Patent Number: 4,996,142

[45] Date of Patent: Feb. 26, 1991

[54] NON-RADIOACTIVE NUCLEIC ACID HYBRIDIZATION PROBES

[75] Inventors: Ali H. Al-Hakim; Roger Hull, both of Norwich, England

[73] Assignee: Agricultural Genetics Company Limited, Cambridge, England

[21] Appl. No.: 94,133

[22] Filed: Sep. 4, 1987

[30] Foreign Application Priority Data

Sep. 4, 1986 [GB] United Kingdom ............... 8621337

[51] Int. Cl.$^5$ .................. C12Q 1/68; C07D 495/04; C08H 1/02; A61K 31/415
[52] U.S. Cl. ........................................ 435/6; 521/31; 526/262; 530/358; 530/401; 536/27; 536/28; 536/29; 548/113; 548/181; 549/32; 549/50; 935/10; 935/77
[58] Field of Search ............... 435/6; 530/358, 401; 521/31; 526/262; 536/27, 28, 29; 935/10, 77; 548/113, 181; 549/32, 50

[56] References Cited

U.S. PATENT DOCUMENTS 4,711,955 12/1987 Ward et al. ........................... 536/29
4,828,979 5/1989 Klevan et al. ........................... 435/6

OTHER PUBLICATIONS

Langer et al. (1981), Proc. Nat'l Acad. Sci. (U.S.A.), vol. 78, No. 11, pp. 6633–6637.
Renz (1983), EMBO J., vol. 2, No. 6, pp. 817–822.

Primary Examiner—Robert A. Wax
Assistant Examiner—Ardin H. Marschel
Attorney, Agent, or Firm—Oblon, Spivak, McClelland, Maier & Neustadt

[57] ABSTRACT

The invention relates to an adduct of a basic macromoleculer and biotin having the general formula:

$$\left[ MM-\left[NH-\left(\underset{\substack{\|\\O}}{C}-alk-NH\right)_m-\underset{\substack{\|\\O}}{C}-(CH_2)_4-\underset{S}{\overset{\substack{HN\overset{\displaystyle O}{\underset{\|}{\,}}NH}}{\bigcirc}}\right]\right]_n$$

in which

MM is the residue of a basic macromolecule formed by substituting the H-atom of one or more primary amino groups;

alk represents an optionally substituted alkylene group having from 1 to 10 C-atoms;

m is 0 or 1; and n is a positive integer, with the proviso that, where MM represents cytochrome C or histone, m is not 0.

The adduct is useful in constructing non-radioactive nucleic acid hydridization probes.

6 Claims, 1 Drawing Sheet

NON-RADIOACTIVE NUCLEIC ACID HYBRIDIZATION PROBES

This invention relates to non-radioactive nucleic acid hybridization probes.

Much of the routine diagnosis of plant viruses is by serological methods. However, these do have some limitations and the possibilities of using nucleic acid hybridization methods have recently become apparent. In this approach nucleic acid from the sample (the target nucleic acid) is immobilized on a solid matrix and is probed with a nucleic acid which has complementary sequences; thus the probe will hybridize to the target.

For detection of the successful hybridization the probe has to have reporter groups. In the original development of the technique the radiolabel $^{32}P$ was used as the reporter group. However it is widely recognised that, for routine use, radiolabels have considerable disadvantages. This has led to the development of some non-radioactive reporter groups. Renz and Kurz (1984) joined peroxidase and alkaline phosphatase directly to the DNA using a linker arm made up from polyethyleneimine, p-benzoquinone and glutaraldehyde. However, these probes are unstable if hybridization is at temperatures greater than 45° C. and such extensive labelling of the probe directly with the enzyme may inferfere with hybridization and thus the final visualisation. The majority of other non-radioactive probes are based on biotin which is detected by its strong affinity to avidin or streptavidin. If an enzyme is linked to the avidin, the reporter group can be detected colorimetrically. Biotin can either be incorporated directly as biotinylated deoxyribonucleotides into the probe (see Langer et al., 1981) or linked to the probe by chemical means. Kempe et al. (1985), and Chollet and Kawashima (1985) have reported methods in which biotin is attached to the 5'-terminus of the DNA molecule. This has the disadvantage that only one biotin molecule is incorporated per DNA molecule. Foster et al. (1985) developed a biotin derivative (termed photobiotin) which, because of its photoactive azide group which on irradiation with light produces very reactive nitrenes, can be linked directly to the heterocyclic bases of nucleic acid.

In another approach a biotin derivative is linked to amide groups of basic proteins (cytochrome C and histones) which in turn are linked by formaldehyde or glutaraldehyde to the DNA or RNA probe (Sodja and Davidson, 1978; Manning et al., 1975; Renz, 1983).

We have developed new methods of linking biotin to nucleic acid which provide a range of lengths of side arm and of numbers of biotin molecules per side arm. This provides a very sensitive probe by which as little as between 10–50fg of target DNA can be visualised using dot-blot hybridization procedures in conjunction with avidin or streptavidin enzyme conjugates.

The present invention provides an adduct of a basic macromolecule and biotin having the general formula:

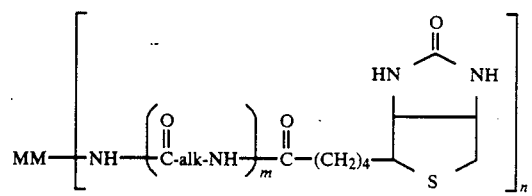

in which

M M is the residue of a basic macromolecule formed by substituting the H-atom of one or more primary amino groups;

alk represents an optionally substituted alkylene group having from 1 to 10 C-atoms;

m is 0 or 1; and n is a positive integer, with the proviso that, where MM represents cytochrome C or histone, m is not 0.

The macromolecule MM is preferably cytochrome C, histone H1 or polyethyleneimine (PEI). Particularly preferred is PEI with a relatively low molecular weight, e.g. from 1000 to 2000.

The group alk is preferably a straight chain alkylene group having from 2 to 8 C-atoms, in particular (—CH$_2$—)$_5$. The integer n is generally from 1 to 30, preferably from 1 to 20.

The adduct according to the invention can be prepared by reacting the basic macromolecule MM with a biotin derivative having the following general formula

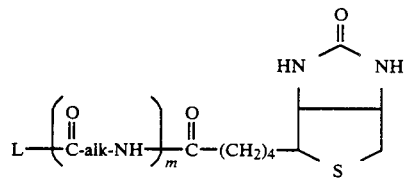

in which alk and m are as defined above, and L is a leaving group.

The biotin derivative undergoes nucleophilic substitution with —NH$_2$ groups on the macromolecule. Preferred leaving groups L are succinimide derivatives, e.g. succinimidyl and sulphonosuccinimidyl, having the following formulae:

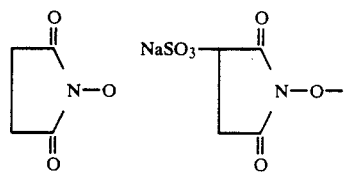

prepared by the reaction of N-hydroxysuccinimide or its sulpho derivative with the appropriate biotin derivative. Other preferred leaving groups are halogen groups, e.g. chlorine and iodine, and halogenated benzene derivatives, e.g. 2,4-dichlorobenzene.

The adduct defined above can be linked by a cross-linking agent to a nucleic acid to form a non-radioactive nuclei acid hybridization probe. Any home-bifunctional cross-linking agent is suitable, and examples include formaldehyde, glutaraldehyde, 1,2,7,8-diepoxyoctane, bis(succinimidyl) suberate and bis (sulphosuccinimidyl) suberate.

The invention also provides a method of detecting the presence of a target nucleic acid having a particular sequence in a sample of nucleic acid, which comprises contacting the sample with a biotin-labelled nucleic acid probe as defined above, said probe being capable of hybridization with the desired sequence; and detecting the resulting hybridization product of target nucleic acid and probe.

The hybridization product can be detected by coupling it with an enzyme, and detecting the action of the coupled enzyme on a suitable substrate.

The enzyme can be coupled to the hybridization product by using a conjugate of the enzyme with avidin or streptavidin. The enzyme is preferably peroxidase or alkaline phosphatase.

The invention further provides a kit for carrying out a method as defined above, comprising a biotin-labelled nucleic acid probe as defined above, and materials for use in detecting the hybridization product of target nucleic acid and probe. The said materials preferably include an enzyme conjugate capable of being coupled to the hybridization product, and a substrate for the enzyme.

Reference is now made to the accompanying,

Figure which shows the structure of a preferred embodiment of hybridization probe according to the invention.

The invention is further illustrated by the following Examples.

DESCRIPTION OF PREFERRED EMBODIMENTS

Figure 1:
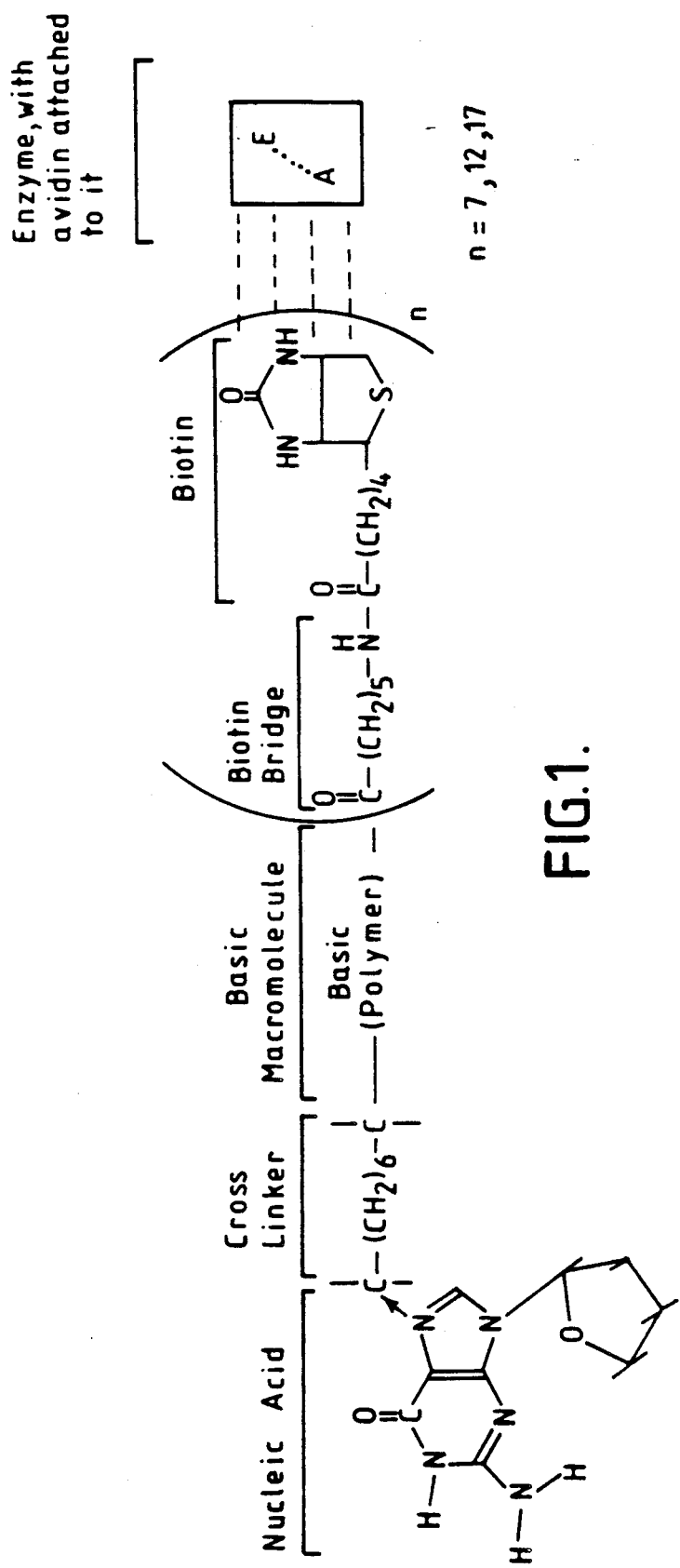

EXAMPLES (a) Preparation of the chemical components of the non-radioactive probes Biotinyl-N-hydroxysuccinimide ester (BHSE) was synthesized by a modification of the method described by Bayer and Wilchek (1980). N,N'-dicyclohexylcarbodiimide (0.4 g) (Aldrich) was dissolved in dimethylformamide solution (6 ml) containing biotin (0.5 g) (Sigma) and N-hydroxysuccinimide (0.3 g) (Sigma). The reaction mixture was stirred overnight at room temperature. The product was filtered and the filtrate was evaporated under reduced pressure (coevaporation with ethyl acetate is recommended) to give a crude crystalline product. The product was washed with diethyl ether and recrystallized from isopropanol/water to give a crystalline white product m.p. 196°–198° C. (75% yield). Biotinylation of histone H1 and cytochrome C was carried out in a manner similar to the Renz (1983) procedure for biotinylation of histone. Histone H1 (Sigma) and cytochrome C (Sigma) were biotinylated separately with BHSE (short chain) and with sulfonosuccinimidyl 6-(biotinamido) hexanoate (SBAH) (Pierce) (long chain) at different ratios. Short chain biotinylated histone H1 and cytochrome C were prepared as follows. 5 $\mu$g, 50 $\mu$g, 250 $\mu$g, 500 $\mu$g and 1 mg of BHSE were each dissolved in 10 $\mu$L of dimethylformamide and added solutions each containing 1 mg histone H1 (in 250 $\mu$l of 50 mM NaHCO$_3$). Similar experiments were performed using cytochrome C instead of histone H1. The solutions were incubated at room temperature for 1 h with frequent mixing and agitating and were then dialyzed overnight against 5 mM sodium phosphate (pH 6.8); the samples were stored at −20° C.

The long chain biotinylated histone H1 and cytochrome C were prepared similarly but using the long chain sulfonosuccinimidyl 6-(biotinamido) hexanoate. This compound is water soluble and thus was added directly to the carbonate solutions instead of being dissolved in dimethylformamide.

Biotinylation of polyethyleneimine

Polyethyleneimine (a 50% solution of the macromolecule with average mol. wt. 60,000 and termed P60) was obtained from Aldrich and Polymin G35 (polyethyleneimine with a mol. wt. of 1400) (termed PG35) was from BASF. P60 and Polymin G35 were biotinylated using various molar ratios of biotin. 5 $\mu$g, 50 $\mu$g, 250 $\mu$g, 500 $\mu$g, 1.4 mg, 2.8 mg, 5.6 mg and 11.2 mg of the long chain biotin derivative, sulfonosuccinimidyl 6-(biotinamido) hexanoate were added to solutions containing 1 mg of polymin in 0.5 ml of 50 mM NaHCO$_3$. The reaction mixtures were incubated at room temperature for 2 h with frequent shaking. The solutions were then dialyzed against 5 mM sodium phosphate (pH 6.8) to remove unreacted biotin derivative and the samples were stored at −20° C.

Target nucleic acid and DNA probes

For the development of these methods a 4–10 kb cDNA to cowpea mosaic virus (CPMV) cloned into M13 was used. Single-stranded and replicative form DNAs were prepared by conventional techniques (Messing, 1983). For negative control calf thymus and salmon sperm DNAs (Sigma) and alfalfa mosaic virus RNA were used.

Cross linking of the biotinylated proteins to DNA

M13 phage ssDNA was cut with Sau3A to give molecules of between 3–4 kb, diluted with sodium phosphate solution (1 pg of DNA+100 $\mu$l of 5 mM phosphate, pH 6.8), denatured by heating (100° C. for 5 min) and cooled on ice. Biotinylated histone H1 or cytochrome C solution (4–5 $\mu$l) was added to the denatured DNA solution followed by addition of 20 $\mu$l of 2.5% of the cross-linking reagent (see Results). The sample was then incubated for 20 min at 37° C. with frequent agitation. After the addition of 5 $\mu$l Orange G (0.025 mg/ml) the product was separated from the unincorporated material by passage through a Sephadex G75 column made in a disposable 1 ml pipette; 5 mM phosphate was used as eluent. The required product was collected in the excluded volume (about 150–200 $\mu$l) which eluted ahead of the Orange G marker and was added directly to the hybridization solution.

(b) Method of Hybridization

Dot-blot hybridization

Nitrocellulose filters (BA85 from Schleicher and Schüll) were marked into 1 cm$^2$ squares, cut to the desired size, soaked in water for 15 min and with 20×SSC for 10 min, placed on Whatman 3 MM paper and spotted (5 $\mu$l) with various amounts of denatured double-stranded target DNA. Since the target DNA was in the covalently closed circular form it was nicked by depurination and alkali treatment. Depurination was in 0.25 N HCl for 15 min at room temperature; alkali treatment was in 0.75 N NaOH, also for 15 min. After neutralization in 0.6 M Na acetate, pH 6, the DNA was denatured by heating to 100° for 2 min. Filters were air dried at room temperature for 15–20 min and baked in a vacuum oven at 80° C. for 2 h. Prehybridization and hybridization was using the conditions of Maule et al.

(1983). A solution of 2.5% dried skimmed milk (Sainsbury plc) (Johnson et al., 1984) was sometimes used as an alternative to Denhardt's solution; it gave similar results. The hybridization solution (2.5 ml for 20 cm$^2$ nitrocellulose sheet) contained 50-250 ng/ml probe.

(c) Detection of hybridized probe

Washing and colorimetric detection

Filters were washed with a solution containing 1% SDS, 2×SSC (250 ml each wash, 4 times×10 min). Filters were incubated in 20 ml 0.1 M Tris-HCl, pH 7.5, 0.1 M NaCl, 2 mM MgCl$_2$, 0.05% Triton X-100 containing 3% bovine serum albumin at room temperature for 1 h. They were then incubated for a further hour in the above buffer containing 1 µg/ml of avidin-peroxidase or avidin alkaline phosphate conjugate (Sigma) with gentle shaking at room temperature. Filters were washed with constant shaking with buffer made of 1 M NaCl, 0.1 M Tris-HCl, pH 7.5, 2.5 mM MgCl$_2$, 0.05% Triton and 1% BSA, 5×5 min), then washed again with a solution of 1 M NaCl, 0.1 M Tris-HCl, pH 9.5, 10 mM MgCl$_2$ 2×10 min.

For colour development, filters which had been incubated with the avidin-peroxidase conjugate, were incubated with 10 ml of 0.1 M Tris-HCl, pH 7.4, 2 ml of ethanol, 6 mg of 3,3'-diansidine and 6 µl of 30% H$_2$O$_2$ or with 4-chloro-1-naphthol in 2 ml methanol+6 µl of 30% H$_2$O$_2$. For detection of alkaline phosphatase, the filters were placed in a solution of 0.1 M Tris-HCl, pH 9.5, 10 mM MgCl$_2$ containing either 0.33 mg/ml nitro blue tetrazolum in 70% dimethylformamide and 0.17 ng/ml of 5-bromo-4-chloro-3-indoyl phosphatase in dimethylformamide (Leary et al., 1983) or 6 mg of 5-chloro-2-toluidin diazonium chloride mixed with naphthol As-Mx phosphate (Bantarri and Goodwin, 1985). All colour development processes were carried out at room temperature in a dark place. Colour reaction was terminated by washing the filters with water; filters can be stored in an envelope of Whatman 3 MM paper.

Determination of amount of biotin linked to PG35

Various amounts (see results) of $^3$H labelled N-hydrosuccinimide biotin (Amersham) were linked to PG35 using BHSF (see above). The unincorporated biotin was removed from that incorporated onto the Polymin on a Sephadex G25 column, the relevant fractions being determined by scintillation counting. Trial spectra showed that Polymin and biotin had an absorbance at 250 nm of 0.284 /mg/ml and 0.111 /mg/ml respectively. The amount of biotin in the biotinylated PG35 fraction was estimated by scintillation counting and the amount of PG35 by the A$_{250nm}$ reading after allowing for the absorbance due to the biotin. The $^3$H labelled biotinylated PG35 was linked to DNA as described above. From scintillation counting and the spectrum of the product the amount of biotinylated PG35 per unit wt of DNA was estimated.

Demonstration of sensitivity of method and utility of the specified components

The various features of the reporter group shown in FIG. 1 were examined in most of the possible combinations (Table 1).

Cross linker

Five bifunctional cross-linking agents, formaldehyde (BDH chemicals), glutaraldehyde (Agar, aids), 1,2,7,8-diepoxyoctane (Aldrich), bis (succinimidyl) suberate (Pierce) and bis (sulphonosuccinimidyl) suberate (Pierce) were compared. These differ in chain length from formaldehyde (1 carbon atom) through glutaraldehyde (5 carbon atoms) to the other three compounds which have 8 carbon atoms. It can be seen from Table 1 that the sensitivity of the test increases with the chain length of the cross-linking agent; there were no significant differences between the three compounds with 8 carbon atoms. However bis (succinimidyl) suberate was not soluble in water and had to be dissolved in dimethyl formamide before use.

Proportion of biotin to histone and cytochrome C:

Renz (1983) showed that when 1 mg histone was reacted with 5 µg and 250 µg short chain biotin (BHSF), 2, 7 and 20 biotin residues respectively were attached to each histone molecule. Analysis of probes made with different proportions of short chain biotin and either histone or cytochrome C (Table 2) shows that 500 µg short chain biotin per mg protein gave the greatest sensitivity without significant non-specific reactions. This proportion was used in subsequent experiments.

No. of biotin molecules incorporated using PG35.

The number of biotin molecules which attached to each molecule of PG35 using different ratios of biotin to polymin were estimated using $^3$H biotin as described in Materials and Methods. Table 3 shows that increasing the ratio of biotin increases the number of biotin molecules attached to PG35.

Analysis of the DNA to which biotinylated PG35 was linked showed that there was one molecule of biotinylated PG35 per 50 nucleotides of DNA. This is slightly more than was found by Renz (1983) (one biotin per 70 nucleotides) for the attachment of biotinylated histone to DNA.

Estimates of the sensitivity of detection using probes containing different amounts of biotin attached to PG35 (Table 3) shows that between 15-20 biotin molecules per molecule of PG35 gave the best results. Ratios higher than this gave non-specific binding.

Basic macromolecule

There was not much difference between the two basic proteins in the sensitivity of the test (Table 1). Of the amino polymers the use of P60 resulted in less sensitivity than that found with the proteins. However incorporation of PG35 into the reporter group gave a greater sensitivity (Table 1).

Biotin side chain

Two side chains supporting biotin were compared. BHSE has 5 carbon atoms whereas SBAH has 11 carbon atoms. Table 1 shows that the length of the side chain had a marked effect on the detection level.

Enzyme

The use of alkaline phosphatase conjugated to avidin proved superior in the sensitivity of detection to peroxidase conjugates (Table 1). The two substrates tested for peroxidase, 3,3'-diansidine, giving a brown product, and 4-chloro-1-naphthol, giving a blue product, did not differ in their sensitivity; the two substrates used for phosphates, nitro blue tetrazolium giving a purple colour and fast red TR salt giving a red colour also did not differ in their sensitivity (results not shown).

Non-specific reactions

Two forms of non-specific reactions were found. In one the whole of the nitrocellulose filter became coloured. This reaction was found using probes F or G (Table 3). In preliminary experiments this nonspecific reaction was shown to also be a considerable problem with nylon membranes (Biodyne Transfer Membrane from Pall) even with probes which gave no background reaction on nitrocellulose. The second type of nonspecific reaction was shown by the control non-homologous DNA or RNA spots. Use of more than 250 ng/ml of polymin or histone or cytochrome C probes gave colour reactions with the control spots but never to the same dilution as the homologous nucleic acid spots.

An assessment of the non-specific reactions of the different probe constructions is given in Table 1.

DISCUSSION

Using a model system we have examined the effects of changes in the various features which make up the reporter group. It is clear that each of the basic features is important.

Two of the features, the cross linker and the biotin side chain, affect the length of the reporter group and from the data shown in Table 1 it can be seen that the longer the reporter group the more sensitive the detection. Briganti et al. (1983), using biotin derivatives of deoxyribonucleotides which were directly incorporated into the probe found that the length of the biotin side chain did not significantly affect the sensitivity on hybridization on nitrocellulose; it did however on in situ hybridization on tissue samples.

The size of the basic macromolecule also had an effect on detection. The sensitivity using the large polyethyleneimine (mol wt 60,000) was much less than that using Polymin G35 (mol wt 1400), cytochrome C (mol wt 12,327) or histone (mol wt 23,000).

It would seem most likely that the degree of sensitivity is limited by steric hindrance. The larger the cross-linker molecule the more basic macromolecules can be linked per unit length of DNA. Steric hindrance between the basic macromolecules also shows up in the lower sensitivity with the larger macromolecule. There can also be steric hindrance at a second level, that between biotin molecules attached to the basic macromolecules.

Of the enzymes tested phosphatase gave the better detection levels. For each enzyme there was no difference between substrate.

The sensitivities achieved in this invention are significantly better than those reported for other systems. Of the biotinylated probes those based on basic protein could detect 5 pg (Renz, 1983) and biotinylated deoxyribonucleotides nick-translated into the probe (Langer et al., 1981) and photobiotin photolinked onto the probe (Foster et al., 1985) could detect 500 fg nucleic acid. Although this photobiotin probe is reported to be very sensitive and highly reliable, the starting material, if used in large quantities, is explosive and the final product (before linking to nucleic acid) is extremely sensitive to light. Non-biotinylated probes such as linking an enzyme directly to the DNA (Renz and Kurz, 1984) or using antibodies to detect N-acetoxy-N-2-acetylaminofluorene linked to the DNA (Tchen et al., 1983) could detect of the order of 1–5 pg nucleic acid. Table 1 shows that some of our probe constructions gave an order of magnitude more sensitivity. These constructions also did not suffer some of the disadvantages of other probe systems. The use of biotinylated deoxyribonucleotides is relatively expensive and requires the process of nick-translation. Photobiotin will decompose on exposure to light and thus has to be kept dark. N-acetoxy-N-2-acetylaminofluorene is a possible carcinogen.

With enzyme colour tests care has to be taken to minimise non-specific reactions. Among the various factors found to be important were the use of the blocking buffer noted in the Examples, extensive washing after incubation with the avidin-enzyme conjugate and the use of clean single-stranded DNA in the prehybridization solution; we routinely phenol extract the calf thymus or salmon sperm DNA. Table 1 shows that the long chain biotin produces less non-specific reaction than does the short chain biotin.

TABLE 1

| Cross-linking reagent | Basic polymer | Side chain | Enzyme | Detection end point (pg) | Non-specific reaction |
|---|---|---|---|---|---|
| F | cyto. C | short | Per. | 500 | ++ |
| F | cyto. C | long | Phos. | 100 | ++ |
| F | Hist. | short | Per. | 500 | ++ |
| F | Hist. | long | Per. | 100 | ++ |
| G | cyto. C | short | Per. | 100 | + |
| G | cyto. C | short | Phos. | 50 | + |
| G | cyto. C | long | Per. | 100 | − |
| G | cyto. C | long | Phos. | 50 | − |
| G | Hist. | short | Phos. | 10 | + |
| G | Hist. | long | Per. | 10-50 | − |
| G | Hist. | long | Phos. | 1 | − |
| D | cyto. C | short | Per. | 10 | − |
| D | cyto. C | short | Phos. | 2 | − |
| D | cyto. C | long | Per. | 10 | − |
| D | cyto. C | long | Phos. | 0.25 | − |
| S | Hist. | short | Per. | 10 | − |
| S | Hist. | short | Phos. | 2 | − |
| S | Hist. | long | Per. | 10 | − |
| S | Hist. | long | Phos. | 0.25 | − |
| G | PEI | short | Phos. | 0.25 | − |
| G | PEI | long | Phos. | 10 | − |
| F | cyto. C | long | Phos. | 100 | ++ |
| G | PG35 | short | Phos. | 1 | − |
| G | PG35 | long | Phos. | 0.01-0.05 | − |
| D | PEI | short | Phos. | 10 | − |
| D | PEI | long | Phos. | 2 | − |
| D | PG35 | short | Phos. | 0.25 | − |
| D | PG35 | long | Phos. | 0.01-0.05 | − |
| S | PEI | short | Phos. | 10 | − |
| S | PEI | long | Phos. | 2 | − |
| F | cyto. C | long | Phos. | 100 | ++ |
| S | PG35 | short | Phos. | 0.05-0.25 | − |
| S | PG35 | long | Phos. | 0.01-0.05 | − |

F = formaldehyde
G = glutaraldehyde
D = 1,2,7,8-diepoxyoctane
S = bis (sulfonosuccinimidyl) suberate
cyto. C = cytochrome C
Hist. = histone HI
Per. = avidin Peroxidase
Phos. = Avidin alkaline phosphatase
− = no reaction with non specific sites
+ = reaction with non specific sites

TABLE 2

Sensitivity of histone/cytochrome C probes with increasing amounts of biotinylated probes

| Amount of biotin ester (µg) | Histone or Cytochrome C (mg) | Sensitivity |
|---|---|---|
| 5 | 1 | 500 pg |
| 50 | 1 | 10-50 pg |
| 250 | 1 | 1-5 pg |
| 500 | 1 | 0.250-0.500 pg |
| 1000 | 1 | non-specific binding |

TABLE 3

Biotinylated polymin probes and their corresponding sensitivities

| | Amount of biotin ester (mg) | Polymin (mg) | No. of biotin attached | Sensitivity (pg) |
|---|---|---|---|---|
| A | 0.005 | 1 | 3 | 5-10 |
| B | 0.05 | 1 | 7 | 1-5 |
| C | 0.250 | 1 | 12 | 0.05-0.5 |
| D | 1.4 | 1 | | |

TABLE 3-continued

| Biotinylated polymin probes and their corresponding sensitivies | | | |
|---|---|---|---|
| Amount of biotin ester (mg) | Polymin (mg) | No. of biotin attached | Sensitivity (pg) |
| E | 2.8 | 1 | 17 | 0.01–0.05 |
| F | 5.6 | 1 | | |
| G | 11.2 | 1 | 20 | reaction with non specific binding sites |

USE OF POLYMIN, POLYBIOTIN PROCESS IN SOUTHERN BLOTS

Materials and Methods

The plasmid pCD4 and the cDNA insert from this clone were prepared as described in Domoney and Casey, 1985. The gene coded within pCD4 corresponds to the pea (Pisum sativum) storage protein vicillin. Preparations of both the plasmid and the insert were the gift of Dr. C Domoney. The insert was labelled with polymin and polybiotin as described previously.

Digestion of the pCD4 clone was carried out with EcoR1 (Boehringer Corp.) as recommended by the manufacturers. Digested samples were ethanol precipitated, resuspended in 10 mM Tris/1 mW EDTA and subjected to electrophoresis on 1% agarose gels for 3–4 hours before transfer to nitrocellulose filters (Southern, 1975).

Subsequent treatment of the filters was as described previously for dot-blots. Briefly, nitrocellulose filters were baked at 80° C. for 2 hours, prehybridized, and hybridized with the biotinylated probe. Hybridization was carried out at 65° C. for 18–20 hours. Filters were washed 4 times (15 mins each) with 250 ml of 2% SSC/0.1% SDS solution at 65° C. and then incubated with blocking solution for 1 hour. This was followed by incubation with avidin alkaline phosphatase (lug/ml) for 1–2 hours. Filters were then washed (4×10 mins) with the above blocking buffer before incubating with the developing reagent (nitro blue tetrazolium and indolyl phosphate).

RESULTS

The polymin, polybiotinylated probe was easily able to detect 10 pg of the plasmid, which represents approximately 2 pg of the target sequence.

REFERENCES

Banttari. E. E. and Goodwin, P. H. (1985). Plant Diseases 69, 202–205.

Bayer, E. A. and Wilchek, M. (1980). Methods Biochem. Anal. 26, 1–45.

Brigati, D. J., Myerson, D., Leary, J. J., Spalholz, B., Travis, S. Z., Fong, C. K., Hsiung, G. D. and Ward, D. C. (1983). Virology 126, 32–50.

Chollet, A. and Kawashima, E. H. (1985). Nucleic Acids Res. 13, 1529–1541.

Foster, A. C., McInnes, J. L., Skingle, D. C. and Symons, R. H. (1985). Nucleic Acids Res. 13, 745–761.

Hull, R. (1984). Trends in Biotechnology 2, 88–91.

Hull, R. (1985). The potential for using dot blot hybridization of plant viruses. In: Development and applications of virus testing. R. A. C. Jones and L. Torrance (Eds.), Association of Applied Biologists (in press).

Hull, R. (1986). BCPC MONO No. 34, 123–129.

Johnson, D. A., Gautsch, J. W., Sportsman, J. R. and Elder, J. H. (1984). Genes Anal. Techn. 1, 3–8.

Kempe, T., Sundquist, W. I., Chow, F. and Hu, S. (1985). Nucleic Acids Res. 13 45–57.

Langer, P. R., Waldrop, A. A. and Ward, D. C. (1981). Proc. Natl. Acad. Sci. USA 78, 6633–6637.

Leary, J. J., Brigatti, D. J. and Ward, D. C. (1983). Natl. Acad. Sci. USA 80, 4045–4049.

Manning, J. E., Hershey, N. D., Broker, T. R., Pellegrini, M., Mitchell, H. K. and Davidson, N. (1975). Chromosoma 53, 107–117.

Maule, A. J., Hull, R. and Donson, J. (1983). Journal of Virological Methods 6, 215–224.

Messing, J. (1983). Methods Enzymol. 101, 20–78.

Owens, R. A. and Diener, T. O. (1981). Science 213, 670–672.

Owens, R. A. and Diener, T. O. (1984). In Methods in Virology, Vol. 7. Eds.

Renz, M. (1983). EMBO J. 2, 817–822.

Renz, M. and Kurz, C. (1984). Nucleic Acids Res. 12, 3435–3444. Eds. K. Maramorosch and H. Koprowski, Academic Press, New York, 173–187.

Singer, B. (1975). Progress in Nucl. Acids Res. and Anal. Biol. 15, 209–284.

Sodja, A. and Davidson, N. (1978). Nucleic Acids Res. 5, 385–401.

Tschen, P., Fuchs, R. P. P., Sage, E. and Leng, M. (1984). Proc. Natl. Acad. Sci. USA 81, 3466.

Domoney, C. and Casey, R. (1985) Nucleic Acids Research 13, 687–699.

Southern, E. M. (1975) Journal of Molecular Biology 98, 503–517.

We claim:

1. An adduct of a basic macromolecule and biotin having the formula:

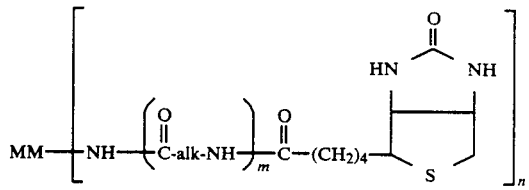

wherein MM is the residue of a basic macromolecule selected from the group consisting of cytochrome C, histone and polyethyleneimine, formed by substituted the H-atom of one or more primary or secondary amino groups; alk represents an alkylene group having from 1 to 10 C-atoms; m is 0 or 1, and n is a positive integer from 1 to 30, with the proviso that, where MM represents cytochrome C or histone, m is not zero.

2. The adduct according to claim 1, wherein macromolecule MM is cytochrome C or histone.

3. The adduct according to claim 1, wherein macromolecule MM is polyethyleneimine (PEI).

4. A biotin-labelled nucleic acid, comprising: the adduct of claim 1 linked to a nucleic acid by a cross-linking agent selected from the group consisting of formaldehyde, glutaraldehyde, 1, 2, 7, 8-diepoxyoctane, bis(succinimidyl) suberate and bis(sulphosuccinimidyl) suberate.

5. An adduct according to claim 3, in which the PEI has a molecular weight of from 1000 to 2000.

6. An adduct according to claim 1, in which alk is $(-CH_2-)_5$.

* * * * *